(12) United States Patent
Fujii et al.

(10) Patent No.: US 11,487,101 B2
(45) Date of Patent: Nov. 1, 2022

(54) ENDOSCOPE OBJECTIVE LENS UNIT AND ENDOSCOPE

(71) Applicant: HOYA CORPORATION, Tokyo (JP)

(72) Inventors: Hiroaki Fujii, Tokyo (JP); Sachiko Nasu, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 380 days.

(21) Appl. No.: 16/646,355

(22) PCT Filed: Sep. 7, 2018

(86) PCT No.: PCT/JP2018/033292
§ 371 (c)(1),
(2) Date: Mar. 11, 2020

(87) PCT Pub. No.: WO2019/054309
PCT Pub. Date: Mar. 21, 2019

(65) Prior Publication Data
US 2020/0285040 A1  Sep. 10, 2020

(30) Foreign Application Priority Data

Sep. 12, 2017  (JP) .............................. JP2017-174970

(51) Int. Cl.
*G02B 21/02* (2006.01)
*G02B 23/24* (2006.01)
(Continued)

(52) U.S. Cl.
CPC ........ *G02B 23/243* (2013.01); *A61B 1/00096* (2013.01); *A61B 1/00163* (2013.01);
(Continued)

(58) Field of Classification Search
CPC .... G02B 23/243; G02B 13/04; G02B 15/177; A61B 1/00096; A61B 1/00163; A61B 1/05
(Continued)

(56) References Cited

U.S. PATENT DOCUMENTS 8,094,382 B2   1/2012   Agatsuma
8,164,839 B2   4/2012   Nasu
(Continued)

FOREIGN PATENT DOCUMENTS

JP          4245985 B2     4/2009
JP       2012-168245 A     9/2012
(Continued)

OTHER PUBLICATIONS

International Search Report issued in International Patent Application No. PCT/JP2018/033292, dated Nov. 13, 2018.
(Continued)

*Primary Examiner* — William Choi
(74) *Attorney, Agent, or Firm* — Greenblum & Bernstein, P.L.C.

(57) ABSTRACT

The objective lens unit includes, a front lens group having a negative refractive power, a diaphragm, and a rear lens group having a positive refractive power, in order from an object side. The front lens group includes a negative lens having a concave surface facing an image surface side, and a positive lens having a convex surface facing the object side, and the rear lens group includes a positive lens having a convex surface facing the image surface side and a cemented lens in which a positive lens and a negative lens are cemented. The endoscope objective lens unit satisfies $-1.6 < f_F/f_R < -1.2$ and $-1.3 < f_3/f_F < -0.7$. Note that $f_F$ and $f_R$
(Continued)

are focal lengths of the entire system of the front lens group and the rear lens group, and $f_3$ is a focal length of a positive lens, in the rear lens group.

5 Claims, 5 Drawing Sheets

(51) Int. Cl.
  *A61B 1/00*    (2006.01)
  *A61B 1/05*    (2006.01)
  *G02B 13/04*   (2006.01)
  *G02B 15/177*  (2006.01)

(52) U.S. Cl.
  CPC ................ *A61B 1/05* (2013.01); *G02B 13/04* (2013.01); *G02B 15/177* (2013.01)

(58) Field of Classification Search
  USPC ................................................ 359/659, 661
  See application file for complete search history.

(56) References Cited

U.S. PATENT DOCUMENTS

| | | |
|---|---|---|
| 8,498,057 B2 | 7/2013 | Nakamura |
| 8,715,170 B2 | 5/2014 | Kanazawa et al. |
| 8,767,320 B2 | 7/2014 | Fujii |
| 9,140,888 B2 | 9/2015 | Fujii |
| 10,036,883 B2 | 7/2018 | Fujii |
| 10,082,648 B2 | 9/2018 | Usui et al. |
| 10,088,666 B2 | 10/2018 | Nasu et al. |
| 10,209,506 B2 | 2/2019 | Fujii et al. |
| 2004/0240081 A1 | 12/2004 | Saito |
| 2011/0002052 A1 | 1/2011 | Nasu |
| 2013/0317299 A1 | 11/2013 | Fujii |
| 2014/0198398 A1 | 7/2014 | Kanazawa et al. |
| 2016/0154230 A1 | 6/2016 | Katakura |
| 2016/0238832 A1 | 8/2016 | Sasamoto |
| 2017/0235123 A1 | 8/2017 | Kamo |
| 2017/0303774 A1 | 10/2017 | Nasu |
| 2018/0149838 A1 | 5/2018 | Takakubo et al. |
| 2019/0053695 A1 | 2/2019 | Fujii et al. |

FOREIGN PATENT DOCUMENTS

| | | | | |
|---|---|---|---|---|
| WO | WO-2012108177 A1 | * | 8/2012 | ......... A61B 1/00174 |
| WO | 2012/176667 A1 | | 12/2012 | |
| WO | 2015/025843 A1 | | 2/2015 | |
| WO | 2015/064614 A1 | | 5/2015 | |
| WO | 2016/204000 A1 | | 12/2016 | |

OTHER PUBLICATIONS

U.S. Appl. No. 16/645,973 to Hiroaki Fujii et al., filed Mar. 10, 2020.

Office Action issued in China Counterpart Patent Appl. No. 201880059105.0, dated Jun. 11, 2021.

* cited by examiner

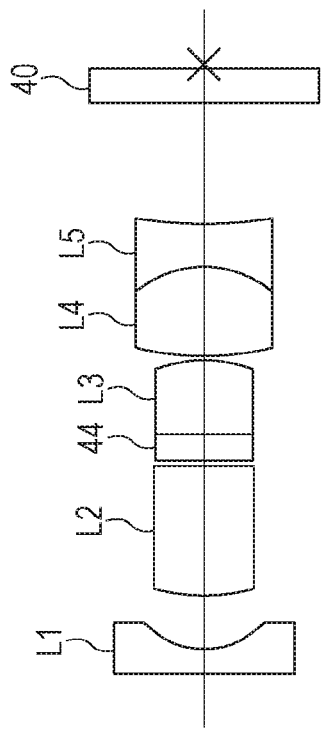
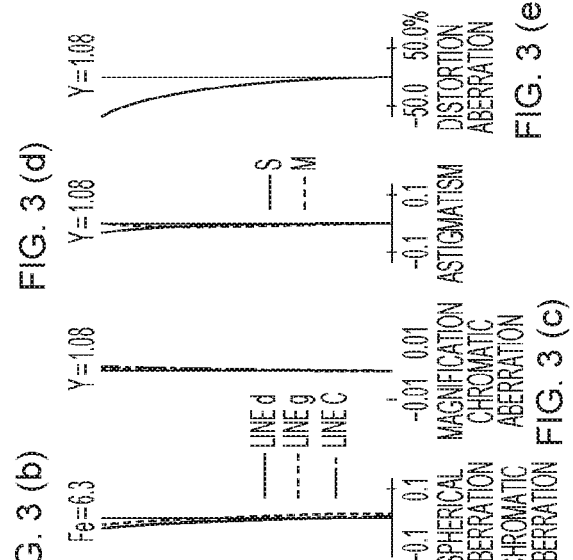
FIG. 3 (a), FIG. 3 (b), FIG. 3 (c), FIG. 3 (d), FIG. 3 (e)
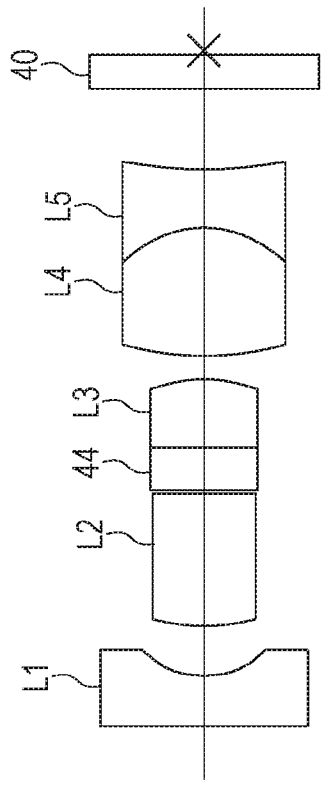
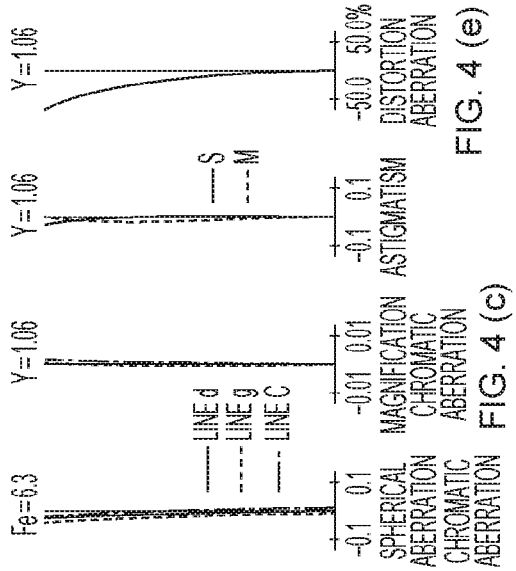
FIG. 4 (a), FIG. 4 (b), FIG. 4 (c), FIG. 4 (d), FIG. 4 (e)

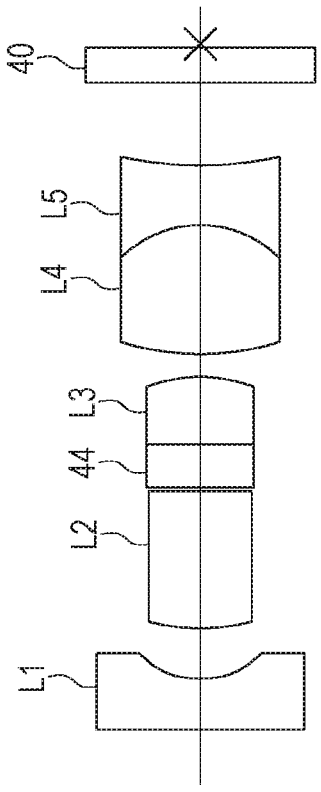
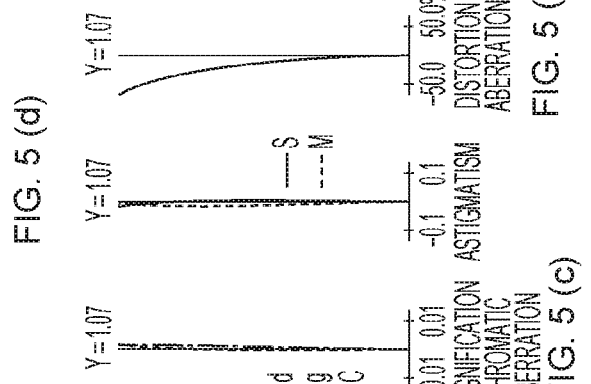
FIG. 5 (a)
FIG. 5 (b) FIG. 5 (c) FIG. 5 (d) FIG. 5 (e)
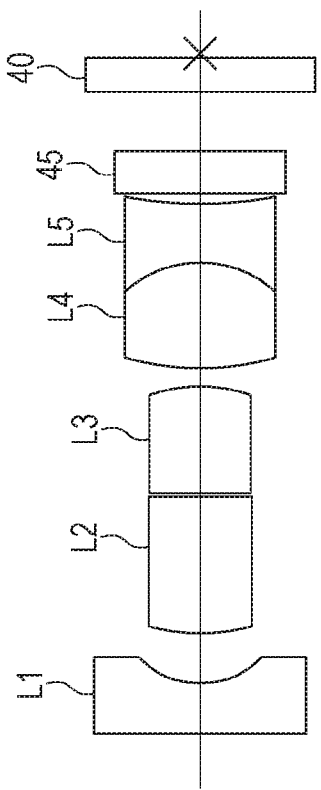
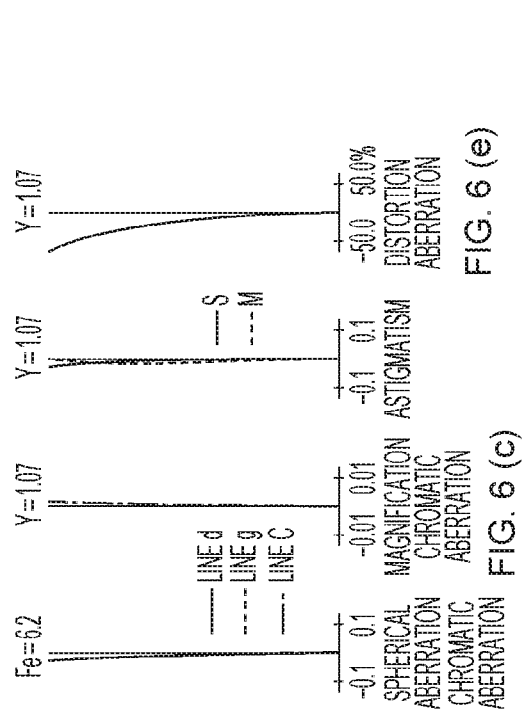
FIG. 6 (a)
FIG. 6 (b) FIG. 6 (c) FIG. 6 (d) FIG. 6 (e)

ENDOSCOPE OBJECTIVE LENS UNIT AND ENDOSCOPE

TECHNICAL FIELD

The present invention relates to an endoscope objective lens unit and an endoscope.

BACKGROUND ART

Today, endoscopes are used to examine biological tissue inside a human body. An endoscope includes an image sensor that captures an image of a biological tissue illuminated with illumination light and an objective lens unit attached to the image sensor, at a distal end portion that is inserted into a human body. Since the objective lens unit needs to be very small and have high optical performance in order to reduce the size of the distal end portion, it is often configured with a small number of lenses.

For example, there is a known endoscope objective lens that includes a front lens group, a diaphragm, and a rear lens group in order from an object side, in which the front lens group is composed of a negative lens and a positive lens having a surface with a small curvature radius on the object side in order from the object side, and the rear lens group is composed of a positive lens having a surface with a small curvature radius on the image side and a cemented lens in which a positive lens and a negative lens are cemented, and there is a predetermined relationship between a focal length f of the entire system and a focal length $f_3$ of the positive lens in the rear lens group (Patent Document 1).

According to the above endoscope objective lens, it is said that a lens having a wide angle, a small outer diameter, and a low maximum light beam height of the first lens can be provided.

CITATION LIST

Patent Literature

Patent Literature 1: JP 4245985 B2

SUMMARY OF INVENTION

Technical Problem

In a general endoscope system, in many cases, a light source device for illumination light that illuminates a biological tissue is provided in a processor separate from the endoscope, and a distal end portion is composed of a light guide cable extending from the light source device and a light distribution lens provided at an end of the light guide cable. On the other hand, a light source device such as an LED may be mounted at a distal end portion of the endoscope.

FIG. 1 is a diagram illustrating an example of a configuration of a distal end portion of an endoscope system in which a light source device 34 is mounted on a distal end portion 12 of an endoscope. The light source device 34 extends from an operation unit or a processor, and is connected with a power supply control line 36 that supplies power and controls turning on and off. The light source device 34 is provided near an objective lens unit 32. An image sensor 30 is provided on a rear side (opposite side from the front end side) of the objective lens unit 32. In such a configuration, when the objective lens unit 32 is miniaturized in order to further reduce the size of the distal end portion 12, the outer diameter of the objective lens unit 32 is reduced and this also shortens the length of the objective lens unit 32 along the optical axis. The image sensor 30 is disposed on the rear side of the objective lens unit 32 whose length is shortened. However, when the image sensor 30 is arranged on the more distal end side so that the image formed by the objective lens unit 32 can be received by the image sensor 30, there is a case where the image sensor 30 cannot be arranged due to interference with the light source device 34. Even when the image sensor 30 can be arranged on the front end side, there may be a case where the related member including a cooling unit for cooling the light source device 34 interferes with the image sensor 30 because the objective lens unit 32 is shortened and a space for providing the related member cannot be secured.

Therefore, the present invention has an object to provides an endoscope objective lens unit having an elongated configuration so that a light source device and related members can be disposed at a distal end portion of an endoscope while maintaining good optical performance, and an endoscope including the endoscope objective lens.

Solution to Problem

One embodiment of the present invention is an endoscope objective lens unit. Hereinafter, reference numerals of corresponding parts in the embodiment illustrated in FIG. 2 are shown in parentheses as an example. The endoscope objective lens unit includes at least a front lens group having a negative refractive power (front lens group G1), a diaphragm (diaphragm 42), and a rear lens group having a positive refractive power (rear lens group G2), in order from an object side.

The front lens group (front lens group G1) includes at least a negative lens (negative lens L1) having a concave surface facing an image side and a positive lens (positive lens L2) having a convex surface on the object side, and the rear lens group (rear lens group G2) includes at least a positive lens (positive lens L3) having a convex surface facing the image surface side, and a cemented lens in which a positive lens (positive lens L4) and a negative lens (negative lens L5) are cemented (cemented lens 46).

In a case where a focal length of the front lens group (front lens group G1) is $f_F$, a focal length of the rear lens group (rear lens group G2) is $f_R$, and a focal length of the positive lens (positive lens L3), in the rear lens group (rear lens group G2), closest to the diaphragm (diaphragm 42) is $f_3$, following expressions (1) and (2) are satisfied.

$$-1.6 < f_F/f_R < -1.2 \qquad (1)$$

$$-1.3 < f_3/f_F < -0.7 \qquad (2)$$

In a case where an average focal length of the positive lens in the endoscope objective lens unit is $f_P$ and a focal length of the entire system of the endoscope objective lens unit is f, a following expression (3) is preferably satisfied.

$$f_P/f < 2.5 \qquad (3)$$

When the focal length of the positive lens (positive lens L2) in the front lens group (front lens group G1) is $f_2$, and the focal length of the entire system of the endoscope objective lens unit is f, the following expression (4) is preferably satisfied.

$$2.0 < f_2/f < 3.0 \qquad (4)$$

The front lens group preferably includes a negative lens (negative lens L1) and a positive lens (positive lens L2) arranged in order from the object side.

In the rear lens group (rear lens group G2), the positive lens (positive lens L3) having the convex surface facing the image side preferably has a plane surface on the object side, the cemented lens (cemented lens 46) is preferably a lens having a configuration in which the positive lens (positive lens IA) having a convex surface facing the object side and the negative lens (negative lens L5) having a concave surface facing the image surface side are cemented, and the rear lens group (rear lens group G2) preferably includes the positive lens (positive lens L4) having the convex surface facing the image surface side and the cemented lens (junction lens 46), in order from the object side.

Another aspect of the present invention is an endoscope. The endoscope includes the endoscope objective lens unit, an image sensor for receiving an object image formed by the endoscope objective lens unit, and a light source unit that illuminates the object.

Advantageous Effects of Invention

According to the endoscope objective lens unit described above, an endoscope objective lens unit is realized to be configured elongated so that a light source device and related members can be arranged at the distal end portion of the endoscope while maintaining good optical performance.

BRIEF DESCRIPTION OF DRAWINGS

FIGS. 3(a) to 3(e) are diagrams illustrating a lens configuration diagram and various aberration diagrams of a first embodiment.

FIGS. 4(a) to 4(e) are diagrams illustrating a lens configuration diagram and various aberration diagrams of a second embodiment.

FIGS. 5(a) to 5(e) are diagrams illustrating a lens configuration diagram and various aberration diagrams of a third embodiment.

FIGS. 6(a) to 6(e) are diagrams illustrating a lens configuration diagram and various aberration diagrams of a fourth embodiment.

DESCRIPTION OF EMBODIMENTS

Figure 1:
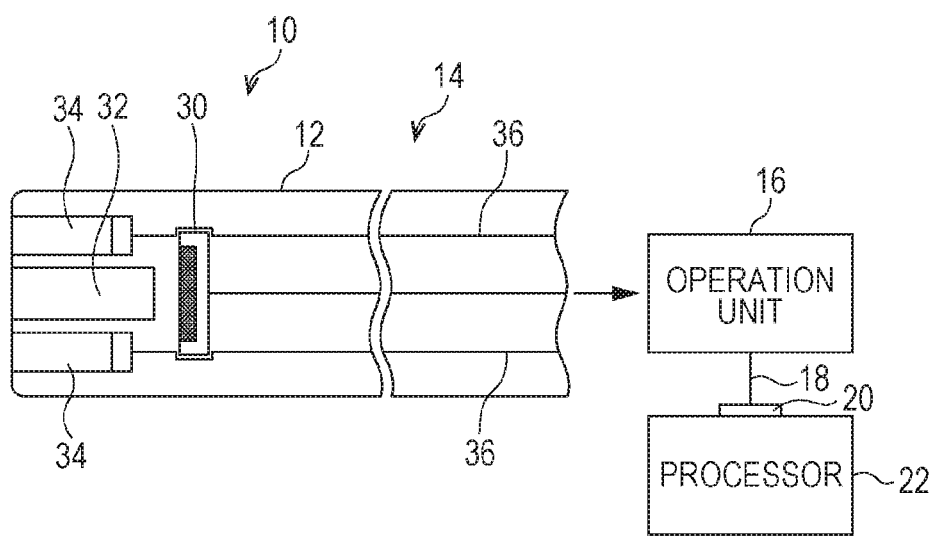
FIG. 1 is a diagram schematically illustrating an example of a configuration of an endoscope equipped with an endoscope objective lens unit.

Hereinafter, an endoscope objective lens unit and an endoscope according to embodiments will be described with reference to the drawings. FIG. 1 is a diagram schematically illustrating an example of a configuration of an endoscope equipped with an endoscope objective lens unit.

An endoscope 10 mainly includes a distal end portion 12, a first flexible tube 14, an operation unit 16, a second flexible tube 18, and a connector 20.

The distal end portion 12 includes at least an image sensor 30 that receives light from an image of a biological tissue and captures the image, an objective lens unit 32 that forms an image of the biological tissue on an imaging surface of the image sensor 30, and a light source unit 34 that is provided near the objective lens unit 32 and illuminates the biological tissue. In addition, the distal end portion 12 may include an ultrasonic diagnostic probe, an opening for discharging fluid such as water or air, or sucking liquid on the biological tissue.

The first flexible tube 14 includes therein at least a signal line for transmitting an imaging signal of the image sensor 30, a power supply control line 36 for operating the image sensor 30 and the light source device 34, and various tubes through which liquid flows.

The operation unit 16 is a part that allows a practitioner to operate the distal end portion 12 so that the distal end portion 12 is placed facing a predetermined position of the biological tissue to observe the biological tissue and treat the biological tissue as necessary.

The second flexible tube 18 includes therein at least a signal line for transmitting a light reception signal of the image sensor 30 and a control line for operating the image sensor 30 and the light source device 34.

A processor 22 processes imaging signals transmitted via the operation unit 16, the second flexible tube 18, and the connector unit 20, generates an image of the biological tissue, and outputs the image. Further, the processor 22 outputs a control signal for controlling operations of the light source device 34 and the image sensor 30.

Figure 2:
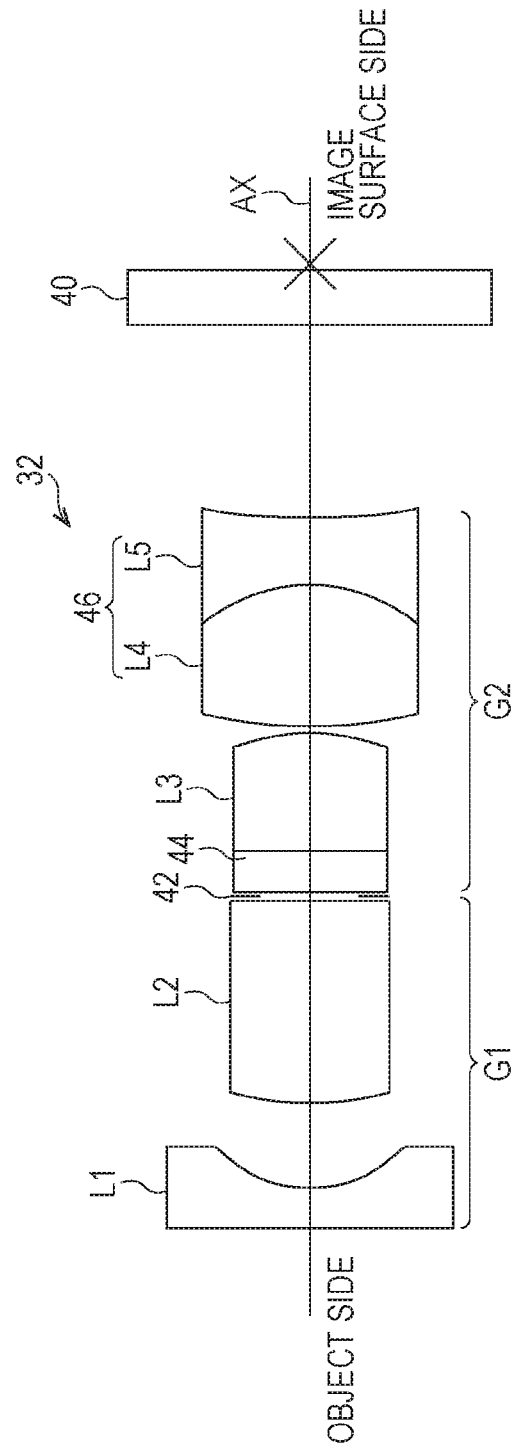
FIG. 2 is a diagram illustrating an example of an arrangement of optical elements of the endoscope objective lens unit according to an embodiment.

At the distal end portion 12, an endoscope objective lens unit (hereinafter referred to as an objective lens unit) 32 having an elongated configuration with which the light source device 34 and related members can be disposed at the distal end portion 12 of the endoscope 10 while maintaining preferable optical performance is used. Hereinafter, the objective lens unit 32 will be described. FIG. 2 is a diagram illustrating an example of the configuration of the objective lens unit 32 according to the present embodiment.

The objective lens unit 32 illustrated in FIG. 2 has at least a front lens group G1, a rear lens group G2, and a diaphragm 42. Each lens constituting each lens group G1, G2 has a rotationally symmetric shape about an optical axis AX of the objective lens unit 32. The diaphragm 42 and an optical filter 44 are provided between the front lens group G1 and the rear lens group G2. Further, a cover glass 40 is provided on the light receiving surface (image surface) side of the image sensor 30 from the rear lens group G2. The cover glass 40 is a component provided on the object side of the image sensor 30. In FIG. 2, the focal position of the objective lens unit 32 is indicated by "x" on the image surface side of the cover glass 40.

The optical filter 44 is a near infrared and infrared cut-off filter.

In the objective lens unit 32, the front lens group G1, a diaphragm 42, and the rear lens group G2 including an optical filter 44 are provided in order from the object side to the image surface side; however, the optical filter 44 is not limited to this order.

Note that the objective lens unit 32 having at least the front lens group G1, the rear lens group G2, and the diaphragm 42 may include the optical filter 44 and the cover glass 40 and a configuration in which an optical element having no optical power is added may be included.

Therefore, in one embodiment, the front lens group G1, the rear lens group G2, the cover glass 40, and the diaphragm 42 are provided. In another embodiment, a front lens group G1, a rear lens group G2, a cover glass 40, a diaphragm 42, and an optical filter 44 are provided. In another embodiment, a front lens group G1, a rear lens group G2, a diaphragm 42, and an optical filter 44 are provided.

The front lens group G1 is a lens group having negative refractive power on the object side with respect to the diaphragm 42. The front lens group G1 includes at least a negative lens L1 having a concave surface facing the image surface side and a positive lens L2 having a convex surface facing the object side. The description that the front lens group G1 includes at least the negative lens L1 and the positive lens L2 means that other lenses having substantially no optical power may be included.

The rear lens group G2 is a lens group having a positive refractive power on the image surface side with respect to the diaphragm 42. The rear lens group G2 includes at least a positive lens L3 having a convex surface facing the image surface side, and a cemented lens 46 in which a positive lens L4 and a negative lens L5 are cemented. The description that the rear lens group G2 includes at least the positive lens L3 and the cemented lens 46 means that other lenses having substantially no optical power may be included.

According to one embodiment, as illustrated in FIG. 2, the negative lens L1 has a plane surface on the object side, the positive lens L2 has a plane surface on the image surface side, the positive lens L3 has a plane surface on the object side, the positive lens L4 has a convex surface on the image surface side and a convex surface on the object side, and the negative lens L5 has a concave surface on the image surface side and a concave surface on the object side.

In the objective lens unit 32 including the front lens group G1 and the rear lens group G2 having such a configuration, when the focal length of the front lens group G1 is $f_F$, the focal length of the rear lens group G2 is $f_R$, and the focal length of the positive lens L3, which is the lens closest to the diaphragm 42 in the rear lens group G2 is $f_3$, the shape, size, and arrangement position of each lens are set to satisfy the following expressions (1) and (2).

$$-1.6 < f_F/f_R < -1.2 \qquad \text{Expression (1):}$$

$$-1.3 < f_3/f_F < -0.7 \qquad \text{Expression (2):}$$

The objective lens unit 32 that satisfies the above expressions (1) and (2) can have an elongated configuration so that related members such as the light source device 34 and a cooling unit can be provided at the distal end portion 12 of the endoscope 10 while maintaining preferable optical performance. At this time, in order for the image sensor 30 at the distal end portion 12 having a small endoscope size to widen the field of view and efficiently image the biological tissue, according to one embodiment, the angle of view is preferably 100 degrees or more and about 170 degrees or less. When the objective lens unit is elongated, the viewing angle generally tends to be narrowed; however, the objective lens unit 32 that satisfies the expressions (1) and (2) can have a wide field of view even made in an elongated shape.

When $f_F/f_R$ is set to $-1.6$ or less, the negative refractive power of the front lens group G1 (hereinafter, the refractive power is referred to as power) becomes weak, and the viewing angle becomes narrower. To widen the viewing angle, the outer diameter of the front lens group G1 may be increased; however, this makes difficult to form the objective lens unit 32 elongated.

On the other hand, when $f_F/f_R$ is set to $-1.2$ or more, the positive power of the rear lens group G2 becomes weak, so the overall length of the objective lens unit 32 becomes long, and this is not preferable when the image sensor 30 and the objective lens unit 32 are arranged at the small distal end portion 12.

From the above point of view, $f_F/f_R$ is less than $-1.2$, preferably $-1.25$ or less, more preferably $-1.3$ or less, and particularly preferably $-1.35$ or less. Further, $f_F/f_R$ is larger than $-1.6$, preferably $-1.55$ or more, and more preferably $-1.51$ or more.

When $f_3/f_F$ is set to $-0.7$ or more, the power of the positive lens L3 closest to the object side in the rear lens group G2 increases, and this may often cause a larger change in the asymmetric image surface curvature of the entire objective lens unit 32 due to the eccentricity of the positive lens L3. Further, since the negative power of the front lens group G1 becomes weak, the focal length of the front lens group G1 becomes long, and accordingly, the focal length of the rear lens group G2 becomes long and the exit pupil distance becomes short. From such a point of view, $f_3/f_F$ is less than $-0.7$, and $f_3/f_F$ is preferably $-0.75$ or less, and more preferably $-0.8$ or less.

On the other hand, when $f_3/f_F$ is set to $-1.3$ or less, since the positive power of the positive lens L3 closest to the object in the rear lens group G2 is weakened, the imaging magnification is increased, and this causes a larger change in the asymmetric image surface curvature of the entire system of the objective lens unit 32 due to the change in the light beam caused by the eccentricity of the front lens group G1. Further, since the negative power of the front lens group G1 is increased, it becomes difficult to correct coma aberration and distortion aberration occurring in the front lens group G1. From such a point of view, $f_3/f_F$ is larger than $-1.3$, preferably $-1.2$ or more, more preferably $-1.1$ or more, and preferably $-1.0$ or more.

Moreover, when the average value (simple average value) of the focal lengths of the positive lenses in the objective lens unit 32 is $f_P$ and the focal length of the entire system of the objective lens unit 32 is f, it is preferable that the shape, size, and arrangement position of each lens are set to satisfy the following expression (3).

$$f_P/f < 2.5 \qquad \text{Expression (3):}$$

When $f_P/f$ is 2.5 or more, the power of the positive lens in the objective lens unit 32 becomes small, and the magnification greatly changes. For this reason, the change in the focal length of the entire system of the objective lens unit 32 caused by the thickness of the positive lens or the change in the distance between the lenses in the front and rear of the optical axis AX direction of the diaphragm 42 becomes large, and this may often cause a large change in the viewing angle. From such a point of view, $f_P/f$ is preferably less than 2.5, more preferably 2.0 or less, and even more preferably 1.9 or less.

Although there is no restriction in the minimum of $f_P/f$, $f_P/f$ is 1.65 or more according to one embodiment, and 1.7 or more according to one embodiment.

In addition, when the focal length of the positive lens L2 in the objective lens unit 32 is set to $f_2$, it is preferable that the shape, size, and arrangement position of the lens are set so as to satisfy the following expression (4).

$$2.0 < f_2/f < 3.0 \qquad \text{Expression (4):}$$

When $f_2/f$ is set 3.0 or more, the power of the positive lens L2 becomes weak, so the negative power of the front lens group G1 increases, and this may often cause a great change in the image surface curvature due to the eccentricity of the front lens group G1. Alternatively, since the magnification of the rear lens group G2 is increased, the change in the focal length of the entire system of the objective lens unit 32 caused by the change in the distance between the lenses in the front and rear of the optical axis AX direction of the diaphragm 42 becomes large, and this may often cause a large change in the viewing angle. From such a point of view, $f_2/f$ is preferably less than 3.0, more preferably 2.9 or less, even more preferably 2.7 or less, and particularly preferably 2.65 or less.

When $f_2/f$ is 2.0 or less, the power of the positive lens L2 of the front lens group G1 becomes stronger, the curvature radius of the convex surface of the positive lens L2 becomes smaller, and the image surface curvature due to the eccentricity of the positive lens itself of the front lens group G1 is increased. From such a point of view, $f_2/f$ is preferably greater than 2.0, more preferably 2.1 or more, even more preferably 2.2 or more, and particularly preferably 2.3 or more.

According to one embodiment, as illustrated in FIG. 2, it is preferable that the negative lens L1 and the positive lens L2 are arranged in order from the object side in the front lens group G1. The positive lens L2 is a positive power lens having a convex surface facing the object side and, since a plane surface can be made to face the image surface side, a change in magnification of the rear lens group G2 due to a change in lens thickness, that is, a change in the field of view can be suppressed.

According to one embodiment, as illustrated in FIG. 2, the positive lens L3 has a plane surface on the object side, and the cemented lens 46 is formed by cementing the positive lens IA with a convex surface on the object side and the negative lens L5 with a concave surface on the image surface side. In other words, the object side surface of the cemented lens 46 is a surface of the positive lens L4 having a convex surface facing the object side, and the image surface side surface of the cemented lens is a surface of the negative lens L5 having a concave surface facing the image surface side. At this time, in the rear lens group G2, it is preferable that the positive lens L3 and the cemented lens 46 including the positive lens L4 and negative lens 5 are arranged in order from the object side.

By making the object side surface of the positive lens L3 a plane surface, a change in magnification of the rear lens group G2 due to a change in lens thickness, that is, a change in the viewing angle can be suppressed. Furthermore, by using a cemented lens 46 that combines a positive lens L4 with the convex surface facing the object side and a negative lens L5 cemented with the positive lens L4, chromatic aberration can be corrected while suppressing changes in the emission angle from the cemented lens 46.

According to one embodiment, preferably, as illustrated in FIG. 2, in the front lens group G1, the lenses L1 and L2 are arranged so that the concave surface on the image surface side of the negative lens L1 and the convex surface on the object side of the positive lens L2 are adjacent to each other so as to face each other and, in the rear lens group G2, the positive lens L3 and the cemented lens 46 are arranged so that the convex surface on the image side of the positive lens L3 and the convex surface on the object side of the positive lens L4 of the cemented lens 46 are adjacent to each other so as to face each other.

First to Fourth Embodiments

Figure 7:
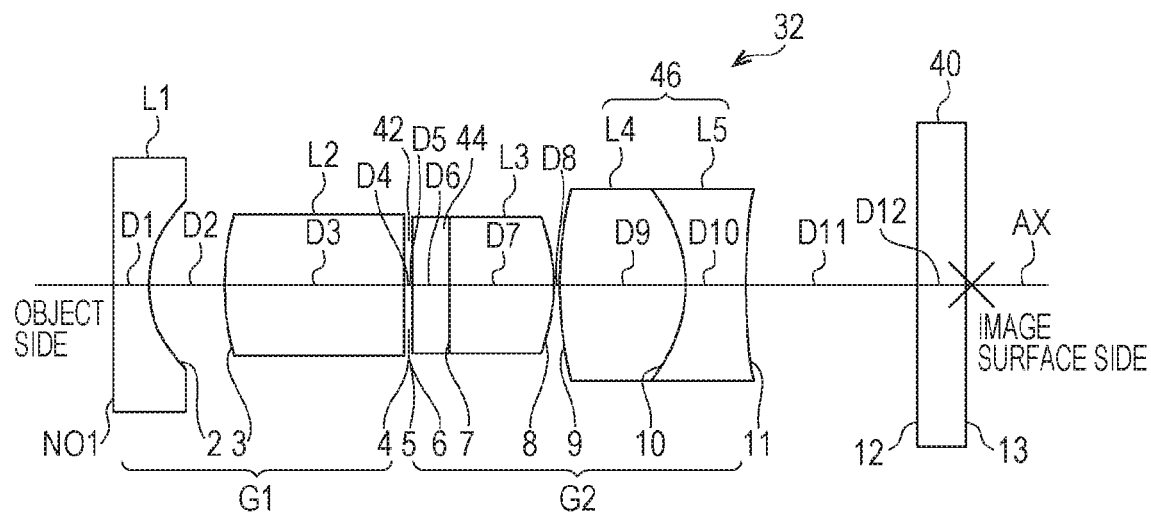
FIG. 7 is a diagram illustrating a configuration in specifications of the first to third embodiments.
Figure 8:
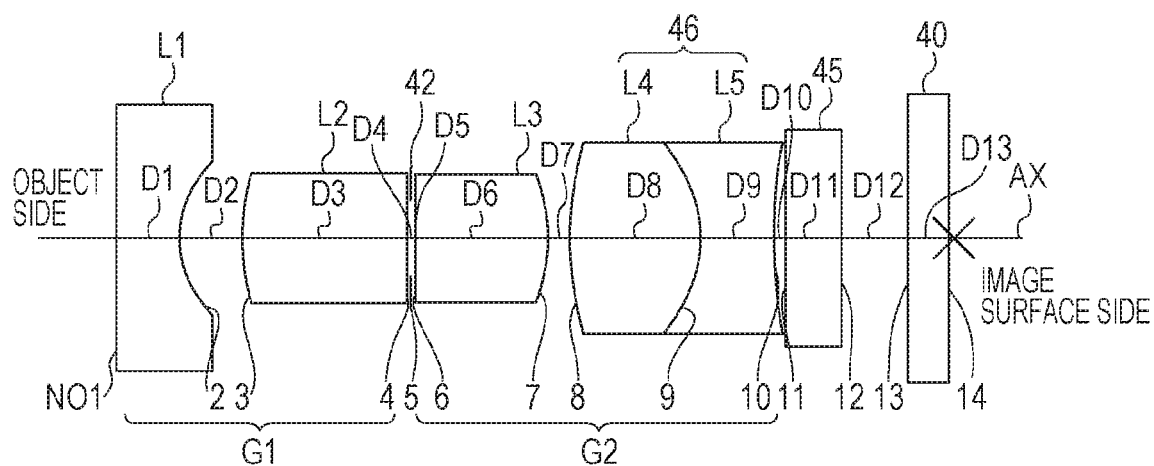
FIG. 8 is a diagram illustrating a configuration according to specifications of the fourth embodiment.

Specific numerical examples of the objective lens unit 32 configured as described above are described in Tables 1 to 4 below (the first to fourth embodiments). On the other hand, a lens configuration diagram and various aberration diagrams of the objective lens unit 32 are illustrated in FIGS. 3 to 6. In FIGS. 3 to 6(a), the diaphragm 42 is not illustrated. FIGS. 3 to 6(b)-(e) illustrate various aberration diagrams of the first to fourth embodiments. The configurations of the first to third embodiments are as illustrated in FIG. 2. FIG. 7 is a diagram illustrating configuration information in the specifications of the first to third embodiments. The lens configuration of the fourth embodiment is as illustrated in FIG. 8. FIG. 8 is a diagram illustrating configuration information in the specification of the fourth embodiment.

Among the aberration diagrams in FIGS. 3 to 6(b)-(e), (b) illustrates spherical aberration and axial chromatic aberration at the line d (588 nm), line g (436 nm), and line C (656 nm). (c) illustrates magnification chromatic aberration at the line d, line g, and line C. In (b) and (c), the solid line indicates the aberration at the line d, the dotted line indicates the aberration at the line g, and the alternate long and short dash line indicates the aberration at the line C. (d) illustrates astigmatism. In (d), the solid line indicates the sagittal component (S), and the dotted line indicates the meridional component (M). (e) illustrates distortion aberration. Fe indicated in the aberration diagrams represents an effective F number. Y represents an image height.

FIGS. 3 to 6(b)-(d), the vertical axis represents the image height (mm), and the horizontal axis represents the aberration amount (mm). FIGS. 3 to 6(e), the vertical axis represents the image height (mm), and the horizontal axis represents the distortion rate.

The specifications of the first embodiment are as described in Table 1 below. FIG. 3(a) illustrates the configuration, and FIGS. 3(b) to 3(e) illustrate various aberration diagrams of the first embodiment. In Table 1, NO represents the surface of the optical element such as the lens, diaphragm, optical filter, cover glass, etc. illustrated in FIG. 7, R represents the curvature radius (mm) of the surface, and D represents the distance (mm) along the optical axis AX from each surface to the surface adjacent to the image surface side. In the curvature radius R, a positive value represents a surface convex toward the object side, and a negative value of R represents a surface convex toward the image surface side. In Table 1, the distances D of NO1 to NO12 are the distances of D1 to D12 defined in FIG. 7. N(d) represents the refractive index at the line d, and νd represents its Abbe number. f in Table 1 represents the focal length (mm) of the entire system of the objective lens unit 32. The first embodiment described in Table 1 includes seven lenses, optical filters, and cover glasses. In Tables 2 and 3, each specification is described in the same format as Table 1.

TABLE 1

| NO | R | D | N(d) | νd |
|---|---|---|---|---|
| 1 | INFINITY | 0.240 | 1.88300 | 40.8 |
| 2 | 0.765 | 0.490 | | |
| 3 | 1.786 | 1.200 | 1.77250 | 49.6 |
| 4 | INFINITY | 0.000 | | |
| 5 Diaphragm | INFINITY | 0.024 | | |
| 6 | INFINITY | 0.240 | 1.52249 | 59.8 |
| 7 | INFINITY | 0.682 | 1.77250 | 49.6 |
| 8 | −1.324 | 0.040 | | |
| 9 | 2.734 | 0.823 | 1.72916 | 54.7 |
| 10 | −1.012 | 0.400 | 1.84666 | 23.8 |
| 11 | 5.849 | 1.109 | | |
| 12 | INFINITY | 0.320 | 1.52249 | 59.8 |
| 13 | INFINITY | — | | |

| | |
|---|---|
| Effective F number Fe | 6.3 |
| Focal length f | 1.00 |
| Magnification | −0.121 |
| Half angle of view (degrees) | 74 |
| Image height (mm) | 1.08 |

The specifications of the second embodiment are as described in Table 2 below. FIGS. 4(b) to (e) illustrate various aberration diagrams of the second embodiment.

TABLE 2

| NO | R | D | N(d) | vd |
|---|---|---|---|---|
| 1 | INFINITY | 0.470 | 1.88300 | 40.8 |
| 2 | 0.783 | 0.456 | | |
| 3 | 1.907 | 1.221 | 1.77250 | 49.6 |
| 4 | INFINITY | 0.000 | | |
| 5 Diaphragm | INFINITY | 0.024 | | |
| 6 | INFINITY | 0.392 | 1.54200 | 63.8 |
| 7 | INFINITY | 0.622 | 1.77250 | 49.6 |
| 8 | −1.450 | 0.217 | | |
| 9 | 2.378 | 1.176 | 1.72916 | 54.7 |
| 10 | −1.064 | 0.549 | 1.84666 | 23.8 |
| 11 | 4.661 | 0.722 | | |
| 12 | INFINITY | 0.314 | 1.52249 | 59.8 |
| 13 | INFINITY | — | | |
| Effective F number Fe | | | 6.3 | |
| Focal length f | | | 1.00 | |
| Magnification | | | −0.122 | |
| Half angle of view (degrees) | | | 72.5 | |
| Image height (mm) | | | 1.06 | |

The specifications of the third embodiment are as described in Table 3 below. FIGS. 5(b) to (e) illustrate various aberration diagrams of the third embodiment.

TABLE 3

| NO | R | D | N(d) | vd |
|---|---|---|---|---|
| 1 | INFINITY | 0.472 | 1.88300 | 40.8 |
| 2 | 0.775 | 0.464 | | |
| 3 | 2.009 | 1.259 | 1.77250 | 49.6 |
| 4 | INFINITY | 0.000 | | |
| 5 Diaphragm | INFINITY | 0.024 | | |
| 6 | INFINITY | 0.394 | 1.54200 | 63.8 |
| 7 | INFINITY | 0.614 | 1.77250 | 49.6 |
| 8 | −1.434 | 0.212 | | |
| 9 | 2.444 | 1.181 | 1.72916 | 54.7 |
| 10 | −1.093 | 0.551 | 1.84666 | 23.8 |
| 11 | 4.436 | 0.767 | | |
| 12 | INFINITY | 0.315 | 1.52249 | 59.8 |
| 13 | INFINITY | — | | |
| Effective F number Fe | | | 6.3 | |
| Focal length f | | | 1.00 | |
| Magnification | | | −0.121 | |
| Half angle of view (degrees) | | | 73.1 | |
| Image height (mm) | | | 1.07 | |

The specifications of the fourth embodiment are as described in Table 4 below. FIG. 6(a) illustrates a configuration, and FIGS. 6(b) to 6(e) illustrate various aberration diagrams of the fourth embodiment. In Table 4, NO represents the surface of the optical element such as the lens, diaphragm, optical filter, cover glass, etc. illustrated in FIG. 8, R represents the curvature radius (mm) of the surface, and D represents the distance (mm) along the optical axis AX from each surface to the surface adjacent to the image surface side. In the curvature radius R, a positive value represents a surface convex toward the object side, and a negative value represents a surface convex toward the image surface side. In Table 4, the distances D of NO1 to NO13 are the distances of D1 to D13 defined in FIG. 8. N(d) represents the refractive index at the line d, and vd represents its Abbe number. In the fourth embodiment illustrated in Table 4, seven optical elements are provided. f represents the focal length (mm) of the entire system of the objective lens unit 32. In the fourth embodiment, as illustrated in FIG. 8, an optical filter 45 is disposed between the negative lens L5 and the cover glass 40 in place of the optical filter 44 illustrated in FIG. 7.

TABLE 4

| NO | R | D | N(d) | vd |
|---|---|---|---|---|
| 1 | INFINITY | 0.472 | 1.88300 | 40.8 |
| 2 | 0.784 | 0.456 | | |
| 3 | 2.014 | 1.258 | 1.77250 | 49.6 |
| 4 | INFINITY | 0.000 | | |
| 5 Diaphragm | INFINITY | 0.024 | | |
| 6 | INFINITY | 0.998 | 1.77250 | 49.6 |
| 7 | −1.370 | 0.157 | | |
| 8 | 2.425 | 0.975 | 1.72916 | 54.7 |
| 9 | −1.045 | 0.550 | 1.84666 | 23.8 |
| 10 | 4.480 | 0.079 | | |
| 11 | INFINITY | 0.393 | 1.54200 | 63.8 |
| 12 | INFINITY | 0.549 | | |
| 13 | INFINITY | 0.314 | 1.52249 | 59.8 |
| 14 | INFINITY | — | | |
| Effective F number Fe | | | 6.2 | |
| Focal length f | | | 1.00 | |
| Magnification | | | −0.121 | |
| Half angle of view (degrees) | | | 72.2 | |
| Image height (mm) | | | 1.07 | |

As can be seen from the aberration diagrams illustrated in FIGS. 3 to 6(b)-(e), it can be evaluated that any of the aberration characteristics of the first to fourth embodiments has preferable characteristics.

The values for the conditional expressions of the first to fourth embodiments are described in Table 5 below.

TABLE 5

| | First embodiment | Second embodiment | Third embodiment | Fourth embodiment |
|---|---|---|---|---|
| $f_F/f_R$ | −1.51 | −1.45 | −1.35 | −1.38 |
| $f_3/f_F$ | −0.82 | −0.97 | −1.02 | −0.97 |
| $f_P/f$ | 1.71 | 1.84 | 1.89 | 1.82 |
| $f_2/f$ | 2.31 | 2.47 | 2.60 | 2.61 |

As described in Table 5, the first to fourth embodiments satisfy the above expressions (1) and (2).

Thus, the objective lens unit satisfying the above expressions (1) and (2) can maintain good aberration characteristics while reducing the diameter of the objective lens unit. Therefore, an elongate configuration in which the light source device 34 and related members can be arranged at the distal end portion 12 of the endoscope is realized.

The endoscope objective lens unit and the endoscope according to the present embodiment have been described above; however, the present invention is not limited to the above described configuration, and various modifications can be made within the scope of the technical idea of the present invention.

REFERENCE SIGNS LIST

10 Endoscope
12 Distal end portion
14 First flexible tube
16 Operation unit
18 Second flexible tube
20 Connector
22 Processor
30 Image sensor
32 Objective lens unit 34 Light source unit
40 Cover glass
42 Diaphragm
44, 45 Optical filter
46 Cemented lens

The invention claimed is:

1. An endoscope objective lens unit, comprising at least a front lens group having a negative refractive power, a diaphragm, and a rear lens group having a positive refractive power in order from an object side, wherein
the front lens group includes at least a negative lens having a concave surface facing an image surface side and a positive lens having a convex surface facing the object side,
the rear lens group includes, in order from the object side, at least a positive lens having a convex surface facing the image surface side and further having a plane surface on the object side, and a cemented lens in which a positive lens having a convex surface facing the object side and a negative lens having a concave surface facing the image surface side are cemented, and
in a case where a focal length of the front lens group is $f_F$, a focal length of the rear lens group is $f_R$, and a focal length of a positive lens, in the rear lens group, closest to the diaphragm is $f_3$, following expressions (1) and (2) are satisfied:

$$-1.6 < f_F/f_R < -1.2; \text{ and} \quad (1)$$

$$-1.3 < f_3/f_F < -0.7. \quad (2)$$

2. The endoscope objective lens unit according to claim 1, wherein, in a case where an average focal length of positive lenses in the endoscope objective lens unit is $f_P$ and a focal length of the entire system of the endoscope objective lens unit is f, a following expression (3) is satisfied:

$$f_P/f < 2.5. \quad (3)$$

3. The endoscope objective lens unit according to claim 1, wherein, in a case where a focal length of the positive lens in the front lens group is $f_2$ and a focal length of the entire system of the endoscope objective lens unit is f, a following expression (4) is satisfied:

$$2.0 < f_2/f < 3.0. \quad (4)$$

4. The endoscope objective lens unit according claim 1, wherein the front lens group has a configuration in which the negative lens and the positive lens are arranged in order from the object side.

5. An endoscope comprising:
the endoscope objective lens unit according to claim 1;
an image sensor that receives an object image formed by the endoscope objective lens unit; and
a light source unit that illuminates the object.

* * * * *